United States Patent
Shibuya et al.

(10) Patent No.: US 9,206,215 B2
(45) Date of Patent: Dec. 8, 2015

(54) HYDROUS CRYSTALLINE 2-O-α-D-GLUCOSYL-L-ASCORBIC ACID, PARTICULATE COMPOSITION COMPRISING THE SAME, THEIR PREPARATION AND USES

(75) Inventors: Takashi Shibuya, Okayama (JP); Seisuke Izawa, Okayama (JP); Shigeharu Fukuda, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 250 days.

(21) Appl. No.: 13/821,498

(22) PCT Filed: Sep. 6, 2011

(86) PCT No.: PCT/JP2011/070681
§ 371 (c)(1),
(2), (4) Date: Mar. 7, 2013

(87) PCT Pub. No.: WO2012/033218
PCT Pub. Date: Mar. 15, 2012

(65) Prior Publication Data
US 2013/0172542 A1    Jul. 4, 2013

(30) Foreign Application Priority Data

Sep. 7, 2010   (JP) .................. 2010-199898

(51) Int. Cl.
| | | |
|---|---|---|
| *C07H 17/04* | (2006.01) | |
| *A61K 31/7048* | (2006.01) | |
| *C07H 19/01* | (2006.01) | |
| *A23L 1/302* | (2006.01) | |
| *A61K 8/60* | (2006.01) | |
| *A61Q 19/00* | (2006.01) | |
| *A61K 9/14* | (2006.01) | |
| *A61Q 19/02* | (2006.01) | |

(52) U.S. Cl.
CPC ............. *C07H 19/01* (2013.01); *A23L 1/302* (2013.01); *A61K 8/602* (2013.01); *A61K 31/7048* (2013.01); *A61Q 19/00* (2013.01); *C07H 17/04* (2013.01); *A61K 9/145* (2013.01); *A61K 2800/10* (2013.01); *A61Q 19/02* (2013.01)

(58) Field of Classification Search
CPC ........................................ C07H 14/04
See application file for complete search history.

(56) References Cited

U.S. PATENT DOCUMENTS

| 5,432,161 A * | 7/1995 | Sakai et al. ............. 514/23 |
| 2011/0091726 A1 * | 4/2011 | Shibuya et al. ........... 428/402 |

FOREIGN PATENT DOCUMENTS

| JP | 3135992 A | 1/1992 |
| JP | 4182413 A | 6/1992 |
| JP | 4182415 A | 6/1992 |
| JP | 5117290 A | 5/1993 |
| JP | 5208991 A | 8/1993 |
| JP | 8333260 A | 12/1996 |
| JP | 2002088095 A | 3/2002 |
| JP | 2004217597 A | 8/2004 |
| WO | 2005034938 A1 | 10/2004 |
| WO | 2006033412 A1 | 9/2005 |
| WO | 2007086327 A1 | 1/2007 |

OTHER PUBLICATIONS

Toyoda et al., "2-O-(alpha-D-Glucopyranosyl)ascorbic Acid, a Novel Ascorbic Acid Analogue Isolated from Lycium Fruit" J. Agric. Food Chem. (2004) vol. 52 pp. 2092-2096.*

* cited by examiner

*Primary Examiner* — Eric Olson
(74) *Attorney, Agent, or Firm* — Browdy and Neimark, PLLC (57) ABSTRACT

The present invention has objects to provide a novel crystalline 2-O-α-glucosyl-L-ascorbic acid and its production process and uses, and solves the above objects by providing hydrous crystalline 2-O-α-glucosyl-L-ascorbic acid, a particulate composition containing hydrous crystalline 2-O-α-glucosyl-L-ascorbic acid, and their production processes and uses.

11 Claims, 2 Drawing Sheets

HYDROUS CRYSTALLINE 2-O-α-D-GLUCOSYL-L-ASCORBIC ACID, PARTICULATE COMPOSITION COMPRISING THE SAME, THEIR PREPARATION AND USES

TECHNICAL FIELD

The present invention relates to hydrous crystalline 2-O-α-D-glucosyl-L-ascorbic acid, a particulate composition containing hydrous crystalline 2-O-α-D-glucosyl-L-ascorbic acid, and their production processes and uses.

BACKGROUND ART

2-O-α-D-Glucosyl-L-ascorbic acid (another name, "ascorbic acid 2-glucoside" throughout the specification, hereinafter) is a compound that is composed of one molecule of D-glucose bound to the hydroxyl group at the C-2 position of L-ascorbic acid (vitamin C) via the α-glucosidic linkage. Unlike L-ascorbic acid, ascorbic acid 2-glucoside is non-reducible and superior in stability and therefore it is also called "stable vitamin C". Ascorbic acid 2-glucoside is readily hydrolyzed by an in vivo enzyme into L-ascorbic acid and D-glucose in living bodies and exerts the physiological activities inherent to L-ascorbic acid.

Ascorbic acid 2-glucoside has been produced on an industrial scale by allowing cyclomaltodextrin glucanotransferase (abbreviated as "CGTase" throughout the specification, hereinafter) to act on a solution containing amylaceous substance and L-ascorbic acid and then allowing glucoamylase to act on the resulting solution (see, for example, Japanese Patent Kokai Nos. 139288/91, 135992/91, 183492/91, 117290/93, and 208991/93; International Patent Publication No. WO01090338; Japanese Patent Kokai No. 2002-088095; International Patent Publication No. WO002010361; and Japanese Patent Kokai No. 2004-065098). A particulate composition containing anhydrous crystalline ascorbic acid 2-glucoside with a purity of at least 98% by weight has been commercialized from Hayashibara Biochemical Laboratories, Inc., Okayama, Japan, as "AA2G", a registered trade mark, for use as a material for cosmetics/quasi-drugs, and it has been also commercialized from Hayashibara Shoji, Co., Okayama, Japan, as "ASCOFRESH", a product name, for use as a material for food products. Ascorbic acid 2-glucoside has been mainly used extensively as a skin-whitening agent, etc., in the fields of cosmetics, quasi-drugs, etc., (see, for example, International Patent Publication No. WO005087182; Japanese Patent Kokai Nos. 046112/92, 182412/92, 182413/92, 182419/92, 182415/92, 182414/92, 333260/96, and 2005-239653; International Patent Publication No. WO006033412; Japanese Patent Kokai Nos. 2002-326924, 2003-171290, and 2004-217597; International Patent Publication No. WO05034938; Japanese Patent Kokai No. 2006-225327; International Patent Publication Nos. WO06137129 and WO06022174; Japanese Patent Kokai No. 2007-063177; and International Patent Publication Nos. WO06132310 and WO07086327).

For reference, anhydrous crystalline ascorbic acid 2-glucoside has been revealed its absolute structure by its single-crystal X-ray structural analysis (see, Carbohydrate Research, Takahiko MANDAI et al., Vol. 232, pp. 197-205, 1992), however, ascorbic acid 2-glucoside has been only known to exist in an anhydrous crystalline form and no other crystal has been known.

DISCLOSURE OF INVENTION

The present invention has objects to provide a novel crystalline ascorbic acid 2-glucoside and its production process and uses.

In the process of investigating the crystallization conditions for ascorbic acid 2-glucoside, the present inventors unexpectedly found that a crystal apparently different from anhydrous crystal of ascorbic acid 2-glucoside is precipitated along with anhydrous crystalline ascorbic acid 2-glucoside under a specific condition. They collected the crystal and subjected it to a powder X-ray diffractometry and revealed that it is a novel crystal that has not been known so far because it exhibited a powder X-ray diffraction pattern different from that of a conventional anhydrous crystalline AA2-2G. It was also revealed that it is a hydrous crystal because it contains a prescribed amount of crystallization water. Further, the present inventors revealed the properties of the novel hydrous crystalline ascorbic acid 2-glucoside and established hydrous crystalline ascorbic acid 2-glucoside, a particulate composition containing the same, and production processes thereof, as well as their uses as fillers/diluents/excipients/vehicles/adjuvant and base materials for pulverizing oily substances, and thus they accomplished the present invention.

The present invention solves the above objects by providing hydrous crystalline ascorbic acid 2-glucoside, a particulate composition containing the same, and their production processes and uses.

According to the present invention, a novel hydrous crystalline ascorbic acid 2-glucoside and a particulate composition containing the same can be produced in large amounts from an aqueous solution containing ascorbic acid 2-glucoside. Since the hydrous crystalline ascorbic acid 2-glucoside and the particulate composition have a satisfactory formativeness, they can be advantageously used in producing shaped products such as granules, tablets, etc. Also, they can be used as base materials for pulverizing oily substances because of their high lipophilicity.

EXPLANATION OF SYMBOLS

Figure 2:
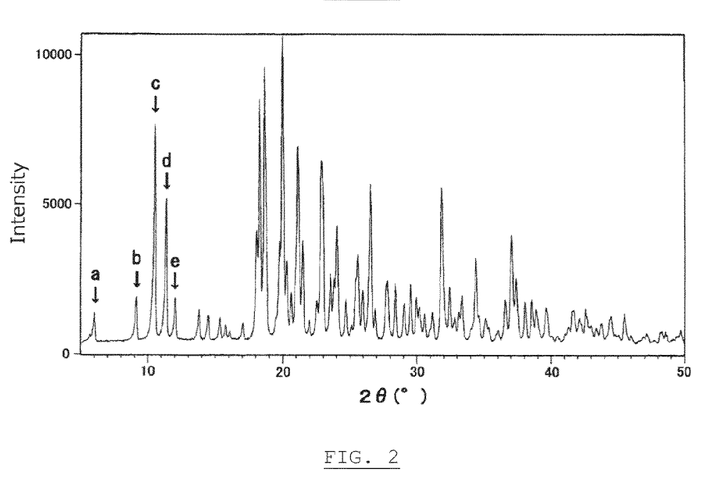
FIG. 2 is a powder X-ray diffraction pattern of a novel crystalline ascorbic acid 2-glucoside.

In FIG. 2, the symbols mean as follows:
↓: A characteristic diffraction peak inherent to a novel crystalline ascorbic acid 2-glucoside;
a: A diffraction peak at a diffraction angle of 6.1°;
b: A diffraction peak at a diffraction angle of 9.2°;
c: A diffraction peak at a diffraction angle of 10.6°;
d: A diffraction peak at a diffraction angle of 11.4°; and
e: A diffraction peak at a diffraction angle of 12.1°

Figure 4:
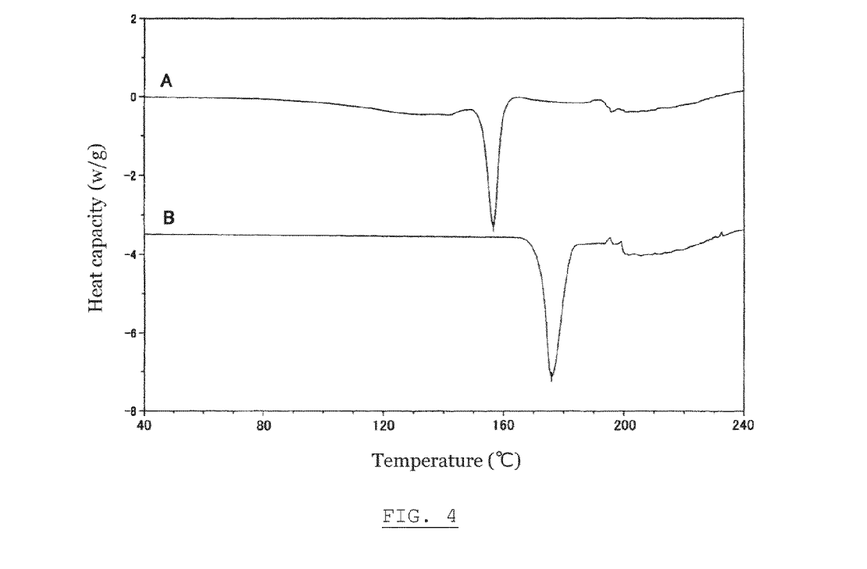
FIG. 4 is a figure of an endothermic pattern of the hydrous crystalline ascorbic acid 2-glucoside of the present invention when determined on differential scanning calorimetric analysis (DSC analysis) compared with that of anhydrous crystalline ascorbic acid 2-glucoside.

In FIG. 4, the symbols mean as follows:

A: An endothermic pattern of the hydrous crystalline ascorbic acid 2-glucoside of the present invention when determined on DSC analysis; and B: An endothermic pattern of anhydrous crystalline ascorbic acid 2-glucoside when determined on DSC analysis.

BEST MODE FOR CARRYING OUT THE INVENTION

The present invention relates to a novel hydrous crystalline ascorbic acid 2-glucoside. As shown in the experiment described later, the hydrous crystalline ascorbic acid 2-glucoside according to the present invention is characterized in that it exhibits characteristic diffraction peaks at least at diffraction angles (2θ) of 6.1°, 9.2°, 10.6°, 11.4° and 12.1°, which are not observed in the powder X-ray diffraction pattern of a conventionally known anhydrous crystalline ascorbic acid 2-glucoside, when subjected to a powder X-ray diffractometry using a CuKα-ray as an X-ray source.

As shown in the experiment described later, the hydrous crystalline ascorbic acid 2-glucoside of the present invention is characterized in that it exhibits a crystallization water content of about 2.7% by weight when analyzed on thermogravimetric analysis (TG analysis). For reference, the value of crystallization water content is distinctly well coincided with 2.66% by weight as a theoretical value of crystallization water content when determined on the assumption that the hydrous crystalline ascorbic acid 2-glucoside of the present invention is a ½ hydrate crystal which contains ½ molecule of crystallization water against a molecule of ascorbic acid 2-glucoside, i.e., $C_{12}H_{18}O_{11} \cdot \frac{1}{2}H_2O$.

Also, as shown in the experiment described later, the hydrous crystalline ascorbic acid 2-glucoside of the present invention is characterized in that it exhibits an endothermic peak at around 156° C. when determined on DSC analysis and that it is clearly distinguished from a conventionally known anhydrous crystalline ascorbic acid 2-glucoside that exhibits a single endothermic peak at around 176° C. upon the same analysis.

Any hydrous crystalline ascorbic acid 2-glucoside is included in the present invention as long as it has the above-identified characteristics and it should never be restricted to a specific one produced by a particular method.

Further, the present invention is also an invention that provides a process for producing the novel hydrous crystalline ascorbic acid 2-glucoside. The origin of ascorbic acid 2-glucoside for use as a material for hydrous crystalline ascorbic acid 2-glucoside should not specifically be restricted and any organic synthetic ones can be used; and, usually, suitably used are high ascorbic acid 2-glucoside content solutions, obtained by conventionally known methods of producing ascorbic acid 2-glucoside for use in food- and cosmetic-materials, i.e., methods of allowing CGTase to act on amylaceous substance and L-ascorbic acid and then allowing glucoamylase to act on the resulting mixture; or particulate compositions containing anhydrous crystalline ascorbic acid 2-glucoside prepared from the above solutions. The present invention does not relate to a process for producing ascorbic acid 2-glucoside per se, and therefore such a process is merely outlined in the below (see Japanese Patent Kokai Nos. 139288/91, 135992/91 and 183492/91 for more information).

For example, a conventional process for producing a particulate composition containing anhydrous crystalline ascorbic acid 2-glucoside basically contains the following steps (1) to (5):

(1) a step of saccharide-transferring reaction by allowing CGTase to act on a solution containing amylaceous substance and L-ascorbic acid to form ascorbic acid 2-glucoside and 2-O-α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid;

(2) a step of glucoamylase treatment by allowing glucoamylase to act on the obtained solution containing 2-O-α-glycosyl-L-ascorbic acids to hydrolyze them up to ascorbic acid 2-glucoside and glucose and to hydrolyze concomitant maltooligosaccharides up to glucose to increase the content of ascorbic acid 2-glucoside;

(3) a step of purification by allowing ascorbic acid 2-glucoside and intact L-ascorbic acid to adsorb on an anion-exchange resin, removing saccharides such as glucose unadsorbed on the resin, eluting ascorbic acid 2-glucoside and L-ascorbic acid with diluted hydrochloric acid, and collecting a fraction rich in ascorbic acid 2-glucoside by a gel filtration chromatography using a strong-acid cation-exchange resin, and then decoloring, filtrating, desalting, and concentrating the resultant;

(4) a step of crystallization by adding a seed crystal of anhydrous crystalline ascorbic acid 2-glucoside to a high ascorbic acid 2-glucoside content solution to precipitate anhydrous crystalline AA-2G to obtain anhydrous crystalline ascorbic acid 2-glucoside; and (5) a step of collecting the obtained anhydrous crystalline ascorbic acid 2-glucoside, and ageing, drying and optionally pulverizing the collected crystals.

The hydrous crystalline ascorbic acid 2-glucoside of the present invention can be relatively easily prepared using, as a material, a particulate composition containing anhydrous crystalline ascorbic acid 2-glucoside produced by the above process (for example, "AA2G", a registered trade mark, with an ascorbic acid 2-glucoside purity of at least 98% by weight, commercialized by Hayashibara Biochemical Laboratories, Inc., Okayama, Japan). The above particulate composition containing anhydrous crystalline ascorbic acid 2-glucoside is placed in a container, suspended in a relatively small amount of refined water, stirred while heating to prepare a supersaturated aqueous ascorbic acid 2-glucoside solution with undissolved anhydrous crystalline ascorbic acid 2-glucoside, and allowed to evaporate water over time in such a manner of allowing it to stand in a constant-temperature chamber or dryer. Thus, the hydrous crystalline ascorbic acid 2-glucoside of the present invention is precipitated in clumps, which differ in appearance from the anhydrous crystal, on the surface of recrystallized anhydrous crystalline ascorbic acid 2-glucoside or the container's wall surface. A particulate composition containing hydrous crystalline ascorbic acid 2-glucoside with an ascorbic acid 2-glucoside purity of at least 98% by weight, on a dry solid basis (d.s.b.) can be obtained by collecting hydrous crystalline ascorbic acid 2-glucoside in clumps, pulverizing the collected clumps, and drying the resultant. The process, however, could only collect a part of the ascorbic acid 2-glucoside, used as a material, as hydrous crystalline ascorbic acid 2-glucoside, and this makes it difficult to efficiently produce hydrous crystalline ascorbic acid 2-glucoside.

While, the hydrous crystalline ascorbic acid 2-glucoside of the present invention can be obtained efficiently from an aqueous solution containing at least 98% by weight of ascorbic acid 2-glucoside, d.s.b., by using the once obtained hydrous crystalline ascorbic acid 2-glucoside as a seed crystal. For example, a block where only hydrous crystalline ascorbic acid 2-glucoside has been precipitated can be obtained by completely dissolving in water a commercialzied particulate composition containing anhydrous crystalline ascorbic acid 2-glucoside ("AA2G", a registered trade mark, with an ascorbic acid 2-glucoside purity of at least 98% by weight, commercialized by Hayashibara Biochemical Laboratories, Inc., Okayama, Japan), optionally concentrating the resulting solution to give a solid concentration of at least 50% w/v, placing the solution in a container, adding hydrous crystalline ascorbic acid 2-glucoside as a seed crystal to the solution in an amount of 1 to 5% by weight, d.s.b., and allowing the resulting mixture to stand at a temperature of 60° C. or lower, preferably, 20 to 50° C. for 0.5 to 7 days under an open system without covering the container with a lid. The block thus obtained can be in conventional manner cut, pulverized, and dried to obtain a particulate composition containing hydrous crystalline ascorbic acid 2-glucoside with an ascorbic acid 2-glucoside content of at least 98% by weight, d.s.b.

Further, the hydrous crystalline ascorbic acid 2-glucoside of the present invention can be also produced directly from an amorphous ascorbic acid 2-glucoside powder with a relatively high purity of ascorbic acid 2-glucoside by using hydrous crystalline ascorbic acid 2-glucoside as a seed crystal as shown in the experiment described later. Such an amorphous ascorbic acid 2-glucoside powder can be obtained, for example, by freeze-drying in vacuo an aqueous solution containing ascorbic acid 2-glucoside with a purity of at least 98% by weight and then pulverizing and drying the resultant. Amorphous ascorbic acid 2-glucoside can be substantially completely converted into the hydrous crystalline ascorbic acid 2-glucoside of the present invention by adding hydrous crystalline ascorbic acid 2-glucoside as a seed crystal to an amorphous ascorbic acid 2-glucoside powder in an amount of at least 30% by weight, ground to homogeneity, mixed, allowed to stand under an environment controlled at a temperature of usually 10 to 40° C., desirably, 20 to 30° C. and a relative humidity of usually 70 to 95%, desirably, 80 to 90% for about 0.5 to about 7 days. The progress for conversion from amorphous ascorbic acid 2-glucoside to hydrous crystalline ascorbic acid 2-glucoside can be confirmed by sampling a part of the powder, subjecting the sample to powder X-ray diffraction diffractometry, and analyzing the obtained powder X-ray diffraction pattern. The hydrous crystalline ascorbic acid 2-glucoside, obtained through the conversion from the amorphous ascorbic acid 2-glucoside powder, can be prepared into a particulate composition containing hydrous crystalline ascorbic acid 2-glucoside by drying directly or after cutting or pulverizing.

The hydrous crystalline ascorbic acid 2-glucoside of the present invention can be also obtained from a solution containing ascorbic acid 2-glucoside with a relatively low purity of ascorbic acid 2-glucoside by using, as a seed crystal, the hydrous crystalline ascorbic acid 2-glucoside obtained by the above process. For example, a massecuite containing hydrous crystalline ascorbic acid 2-glucoside is provided by placing in a crystallizer a solution containing ascorbic acid 2-glucoside with an ascorbic acid 2-glucoside purity of at least 85% by weight, d.s.b., and a concentration of 65 to 90% w/v, obtained through the steps (1) to (3) in the above process for producing a particulate composition containing hydrous crystalline ascorbic acid 2-glucoside; adding a particulate composition containing ascorbic acid 2-glucoside in an amount of 1 to 20% by weight as a seed crystal; and precipitating crystals under stirring conditions at a temperature of 60° C. or lower, desirably, 20 to 50° C. Usually, a solid-liquid separation method is preferably used as a method for collecting a relatively-high-purity hydrous crystalline ascorbic acid 2-glucoside from the massecuite. In the case of such a separation method, the massecuite is usually subjected to a basket-type centrifuge to separate into hydrous crystalline ascorbic acid 2-glucoside and a syrup (a crystallized mother liquid), and optionally, for example, a small amount of cold water or cold ethanol is sprayed to the hydrous crystalline ascorbic acid 2-glucoside for washing to produce a relatively-high-purity hydrous crystalline ascorbic acid 2-glucoside. The purity of ascorbic acid 2-glucoside in the obtained hydrous crystalline ascorbic acid 2-glucoside is usually at least 98% by weight.

In particular, in the case of not requiring a relatively-high-purity hydrous crystalline ascorbic acid 2-glucoside, the above massecuite can be advantageously prepared into a particulate composition containing hydrous crystalline ascorbic acid 2-glucoside by a spray-drying method of spray-drying the massecuite and ageing and drying the resultant. Such a spray-drying method can easily produce a particulate composition containing hydrous crystalline ascorbic acid 2-glucoside with an ascorbic acid 2-glucoside purity of at least 85% by weight by successively providing a massecuite, which has an ascorbic acid 2-glucoside purity of at least 85% by weight, d.s.b., a concentration of 65 to 75% w/v, and a crystallization percentage (a percentage of crystals against the solid contents) of 10 to 60% by weight, obtained through the steps (1) to (4) in the above-mentioned process for producing a particulate composition containing anhydrous crystalline ascorbic acid 2-glucoside; spraying the massecuite, for example, from a nozzle with a high-pressure pump or by a rotatory disk; drying the resultant with hot air having a temperature of not melting the resulting crystalline powder, for example, with 60 to 100° C. hot air; and ageing the resultant by keeping it at a relative humidity of 53 to 90% using 20 to 60° C. hot air for about 1 to about 48 hours.

The above massecuite can be advantageously made into a block which is then subjected to a block pulverization for producing a particulate composition containing hydrous crystalline ascorbic acid 2-glucoside. In the case of such a block pulverization, a particulate composition containing hydrous crystalline ascorbic acid 2-glucoside with an ascorbic acid 2-glucoside purity of at least 85% by weight can be easily produced by providing a massecuite having usually a moisture content of 5 to 20% w/v and a crystallization percentage of about 10 to about 60% by weight, allowing the massecuite to stand for about 0.1 to about 7 days to effect crystallization and solidification to make it into a block as a whole, and pulverizing the block by a method such as cutting or pulverizing before drying.

Further, the present invention is also an invention that provides uses of a hydrous crystalline ascorbic acid 2-glucoside powder and a particulate composition containing hydrous crystalline ascorbic acid 2-glucoside. Varying depending on the particle size distribution, the hydrous crystalline ascorbic acid 2-glucoside powder of the present invention has a characteristic superiority in formativeness to conventionally known particulate compositions containing anhydrous crystalline ascorbic acid 2-glucoside. As shown in the section of the experiment described later, when a conventional particulate composition containing anhydrous crystalline ascorbic acid 2-glucoside is tried to be formed into a tablet with a tabletting machine, the resulting tablet is induced cracking or chipping when a load to the particulate composition is released therefrom, resulting in a difficulty of forming into a tablet; while in the case of the hydrous crystalline ascorbic acid 2-glucoside powder of the present invention, a tablet with a relatively high hardness can be prepared without inducing any cracking and chipping.

The hydrous crystalline ascorbic acid 2-glucoside powder of the present invention has a characteristic that it can be advantageously used as a base material for pulverizing oily substances because it has a relatively higher hydrophilicity with oily substances than conventional particulate compositions containing anhydrous crystalline ascorbic acid 2-glucoside. Such a characteristic can be advantageously used when in producing powdered fats and oils.

The hydrous crystalline ascorbic acid 2-glucoside and the particulate composition containing the same of the present invention are in no way different from conventional particulate compositions containing anhydrous crystalline ascorbic acid 2-glucoside in that they are particulate compositions of ascorbic acid 2-glucoside. Accordingly, the hydrous crystalline ascorbic acid 2-glucoside and the particulate composition containing the same of the present invention can be not only used in the above-identified uses but also extensively incorporated into food products, cigarettes and tobaccos, feeds, baits, cosmetics, pharmaceuticals, shaped products, etc., similarly as in conventional anhydrous crystalline ascorbic acid 2-glucoside, as well as compositions such as livingwares, products for agriculture, forestry and fishery, reagents, and products for chemical industries.

The following experiments concretely explain the present invention.

<Experiment 1: Obtention of Novel Crystalline Ascorbic Acid 2-Glucoside>

To a 500-ml glass beaker were added 20 g of a particulate composition containing anhydrous crystalline ascorbic acid 2-glucoside ("AA2G", a registered trade mark, with an ascorbic acid 2-glucoside purity of at least 98% by weight, commercialzied by Hayashibara Biochemical Laboratories, Inc., Okayama, Japan) and 7.5 g of deionized water, and the resulting mixture was heated to 50 to 60° C. while stirring to prepare a suspension, where undissolved anhydrous crystalline ascorbic acid 2-glucoside partially remained in a supersaturated solution of ascorbic acid 2-glucoside. Thereafter, the beaker with the suspension was placed in a constant-temperature chamber controlled at 40° C. and allowed to stand therein for three days to evaporate the moisture over time, resulting in observing precipitated crystals in clumps, which differed in appearance from anhydrous crystalline ascorbic acid 2-glucoside, on the surface of the layers of anhydrous crystalline ascorbic acid 2-glucoside formed in the bottom of the beaker and on the beaker's wall surface. The crystals in clumps were collected with a scoopula, pulverized and dried to obtain a 3.8 g crystalline powder.

<Experiment 2: Physical Property of Novel Crystalline Ascorbic Acid 2-Glucoside>

Using the crystalline powder obtained in Experiment 1, the following properties were investigated.

<Experiment 2-1: Microscopic Photograph of Novel Crystalline Ascorbic Acid 2-Glucoside>

Figure 1:
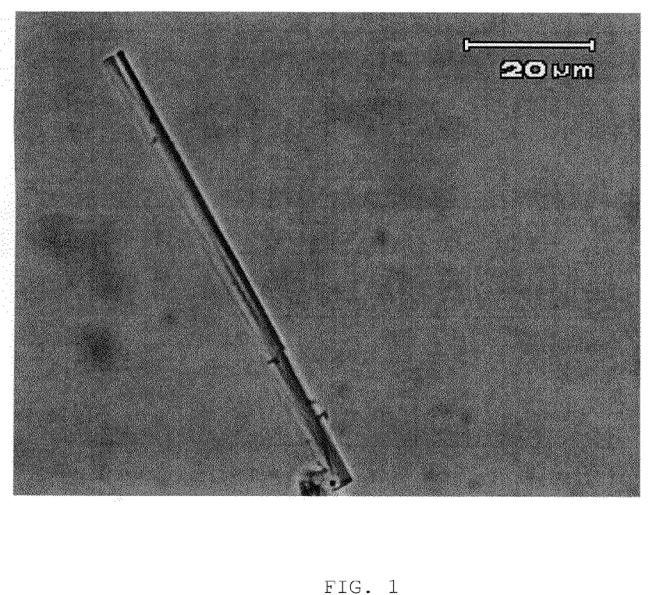
FIG. 1 is a microscopic photograph (1,250 magnifications) of a novel crystalline ascorbic acid 2-glucoside.

An adequate amount of the crystalline powder obtained in Experiment 1 was suspended in glycerol gelatin, commercialized by Sigma-Aldrich Co. LLC., St. Louis, Mo., USA, and the suspension was placed on a slide glass and observed by "BX50", a microscope commercialized by Olympus Corporation, Tokyo, Japan, and photographed by "DP21", a digital camera for microscope, commercialized by Olympus Corporation, Tokyo, Japan. An example of a microscopic photograph of the crystal is in FIG. 1 (1,250 magnifications). As shown in FIG. 1, a prismatic crystal was observed.

<Experiment 2-2: Purity of Novel Crystalline Ascorbic Acid 2-Glucoside>

The crystalline powder obtained in Experiment 1 was dissolved in deionized water to give a final concentration of 0.1 or 1% w/v, and each solution was membrane filtered and subjected to a high-performance liquid chromatography (HPLC) under the following conditions. For reference, "ASCORBIC ACID 2-GLUCOSIDE 999" (Code No.: AG124, Purity: at least 99.9% by weight, a product name of a reagent-grade ascorbic acid 2-glucoside-containing powder, commercialized by Hayashibara Biochemical Laboratories, Inc., Okayama, Japan), was used as a standard specimen of ascorbic acid 2-glucoside and subjected to HPLC analysis similarly as above.

(Conditions for HPLC Analysis)

HPLC Apparatus: "LC-10AD", commercialized by Shimadzu Corp., Kyoto, Japan;

Degasser: "DGU-12AM", commercialized by Shimadzu Corp., Kyoto, Japan;

Column: "WAKOPAK WAKOBEADS T-330", $H^+$-form, commercialized by Wako Pure Chemical Industries, Osaka, Japan;

Sample injection volume: 5 µl of 0.1% solution for UV detector or 20 µl of 1% solution for differential refractometer;

Eluent: 0.01% (v/v) aqueous nitric acid solution;

Flow rate: 0.5 ml/min;

Temperature: 25° C.;

Detector: "UV200-400", a multi-wavelength UV detector, commercialized by Shimadzu Corp., Kyoto, Japan; "RID-10A", a differential refractometer, commercialized by Shimadzu Corp., Kyoto, Japan;

Data processing apparatus: "CHROMATOPAK C-R7A", commercialized by Shimadzu Corp., Kyoto, Japan;

Upon the above HPLC analysis, the crystalline powder obtained in Experiment 1 gave an elution peak at the same retention time (Rt) as the standard specimen of ascorbic acid 2-glucoside by any of the detection methods using the UV detector and the differential refractometer and gave a maximum absorption wavelength (λmax) of 248 nm when detected on the multi-wavelength UV detector, revealing that they were completely coincided with those of the standard specimen of ascorbic acid 2-glucoside. The purity of ascorbic acid 2-glucoside of the crystalline powder obtained in Experiment 1 was 99.5% by weight when calculated based on the peak area of an HPLC chromatogram obtained by using the differential refractometer.

<Experiment 2-3: Powder X-Ray Diffraction of Novel Crystalline Ascorbic Acid 2-Glucoside Powder>

Figure 3:
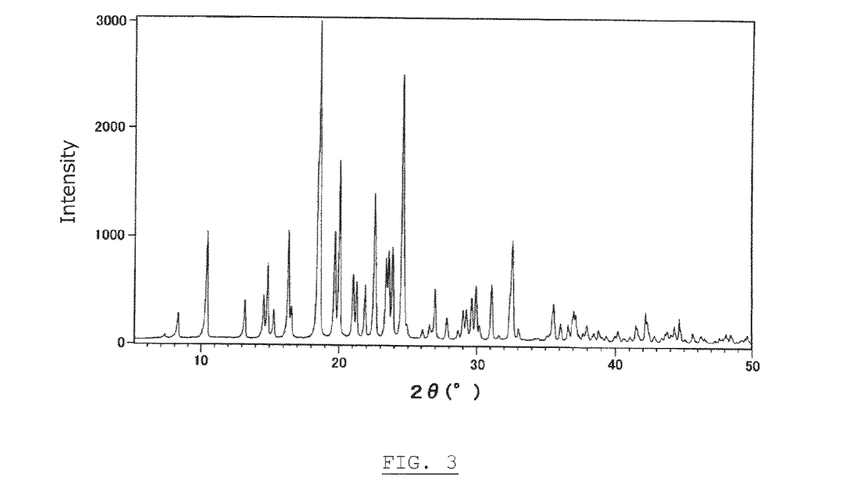
FIG. 3 is a powder X-ray diffraction pattern of a reagent-grade powder containing anhydrous crystalline ascorbic acid 2-glucoside.

About 50 milligrams of the crystalline ascorbic acid 2-glucoside powder obtained in Experiment 1 was placed on a silicon reflection free sample holder and subjected to the following to obtain a powder X-ray diffraction pattern based on a powder X-ray diffraction profile obtained by using "X'Pert PRO MPD", a product name of a commercially available reflected-light powder X-ray diffractometer commercialized by Spectris Co., Ltd., Tokyo, Japan, and irradiating a CuKα-ray (X-ray electric current: 40 mA, X-ray tube voltage: 45 kV, wavelength: 1.5405 Å), as a characteristic X-ray irradiated from a Cu target. FIGS. 2 and 3 are respectively powder X-ray diffraction patterns of the novel crystalline ascorbic acid 2-glucoside powder and the "ASCORBIC ACID 2-GLUCOSIDE 999" (Code No.: AG124, Purity: at least 99.9% by weight, a product name of a reagent-grade ascorbic acid 2-glucoside-containing powder, commercialized by Hayashibara Biochemical Laboratories, Inc., Okayama, Japan), used as a control.

As evident from the comparison of FIG. 2 with FIG. 3, the powder X-ray diffraction pattern of the novel crystalline ascorbic acid 2-glucoside powder obtained in Experiment 1 was completely different from that of the conventional anhydrous crystalline ascorbic acid 2-glucoside powder. Namely, the powder X-ray diffraction pattern of the novel crystalline ascorbic acid 2-glucoside powder showed characteristic diffraction peaks at least at diffraction angles (2θ) of 6.1° (the symbol "a" in FIG. 2), 9.2° (the symbol "b" in FIG. 2), 10.6° (the symbol "c" in FIG. 2), 11.4° (the symbol "d" in FIG. 2), and 12.10 (the symbol "e" in FIG. 2), which were not observed in the powder X-ray diffraction pattern of the conventional anhydrous crystalline ascorbic acid 2-glucoside powder.

<Experiment 2-4: Crystalline Water Content of Novel Crystalline Ascorbic Acid 2-Glucoside Powder>

Three and half milligrams of the crystalline ascorbic acid 2-glucoside powder obtained in Experiment 1 was placed in an aluminum container, retained at 25° C. for three minutes in a nitrogen gas stream at a flow rate of 300 ml/min using "TG/DTA6200", a product name of a simultaneous thermogravimetry and differential thermal analyzer, commercialized by SII NanoTechnology Inc., Chiba, Japan, and subjected to thermogravimetric analysis (TG analysis) while increasing the temperature up to 250° C. at a temperature increasing rate of 10° C./min, resulting in observing a weight reduction of 2.70% by weight as heating from 110 to 145° C. This revealed that the crystalline powder contained 2.70% by weight of crystallization water. From the result, the crystalline ascorbic acid 2-glucoside powder obtained in Experiment 1 was revealed to be a conventionally unknown hydrous crystal. For reference, the value of crystallization water content is distinctly well coincided with 2.66% by weight as a theoretical value for crystallization water content determined on the assumption that the hydrous crystal is a ½ hydrate crystal of ascorbic acid 2-glucoside, i.e., $C_{12}H_{18}O_{11} \cdot \frac{1}{2}H_2O$.

<Experiment 2-5: Elemental Analysis of Novel Crystalline Ascorbic Acid 2-Glucoside Powder>

Five to ten milligrams of the crystalline ascorbic acid 2-glucoside powder obtained in Experiment 1 was weighed and quantified for carbon (C) and hydrogen (H) under the conditions of a reaction temperature of 850° C. and a reduction temperature of 600° C. using "SUMIGRAPH NCH-22F", an NCH quantitative apparatus of oxygen circulating combustion/TCD detection system, commercialized by Sumika Chemical Analysis Service Ltd., Osaka, Japan, to obtain values of 41.53% by weight for carbon and 5.58% by weight for hydrogen. The elemental analysis results were well coincided with 41.50% by weight for carbon and 5.51% by weight for hydrogen as theoretical values determined on the assumption that it is ½ hydrate crystal of ascorbic acid 2-glucoside, i.e., $C_{12}H_{18}O_{11} \cdot \frac{1}{2}H_2O$. From the results in Experiments 2-4 and 2-5, the crystalline ascorbic acid 2-glucoside powder obtained in Experiment 1 was estimated to be in the form of a ½ hydrate crystal. The ascorbic acid 2-glucoside crystal obtained in Experiment 1 is called "hydrous crystalline ascorbic acid 2-glucoside", hereinafter.

<Experiment 2-6: Differential Scanning Calorimetric Analysis (DSC Analysis) of Hydrous Crystalline Ascorbic Acid 2-Glucoside Powder>

Three and half milligrams of the hydrous crystalline ascorbic acid 2-glucoside powder obtained in Experiment 1 was placed in an aluminum container, retained at 25° C. for five minutes in a nitrogen gas stream at a flow rate of 50 ml/min using "DSC Q20", a product name of a differential scanning calorimeter, commercialized by TA Instruments Japan Inc., Tokyo, Japan, and then heated up to 250° C. at a temperature increasing rate of 10° C./min to analyze the endothermic pattern on DSC analysis. The endothermic pattern of the hydrous crystalline ascorbic acid 2-glucoside powder is shown by the symbol "A" in FIG. 4, and that of "ASCORBIC ACID 2-GLUCOSIDE 999" (Code No.: AG124, Purity: at least 99.9% by weight, a product name of a reagent-grade ascorbic acid 2-glucoside-containing powder, commercialized by Hayashibara Biochemical Laboratories, Inc., Okayama, Japan), is shown by the symbol "B" in FIG. 4.

As evident from FIG. 4, the anhydrous crystalline ascorbic acid 2-glucoside powder showed a single endothermic peak involved in melting at around 176° C., while the hydrous crystalline ascorbic acid 2-glucoside powder obtained in Experiment 1 showed a slight endotherm in the range of 110 to 145° C. and an endothermic peak involved in melting at around 157° C., and thus they had completely different endothermic patterns on DSC analysis.

<Experiment 3: Preparation of Hydrous Crystalline Ascorbic Acid 2-Glucoside Powder from Aqueous Solution Containing High-Purity Ascorbic Acid 2-Glucoside>

In Experiment 1, a novel hydrous crystalline ascorbic acid 2-glucoside was obtained from a supersaturated aqueous solution of a relatively-high purity ascorbic acid 2-glucoside, where undissolved anhydrous crystalline ascorbic acid 2-glucoside coexisted. In this experiment, the conditions for producing such a novel hydrous crystalline ascorbic acid 2-glucoside was further investigated using an aqueous solution containing a relatively-high purity ascorbic acid 2-glucoside.

Two hundred grams of "AAG", a product name of a particulate composition containing anhydrous crystalline ascorbic acid 2-glucoside with a purity of at least 98% by weight, commercialized by Hayashibara Biochemical Laboratories, Inc., Okayama, Japan, was added to 200 ml of refined water, and completely dissolved therein by heating and stirring. The aqueous solution was transferred to a tray with 20-cm-square and 5-cm-depth, admixed with 2.0 g of the hydrous crystalline ascorbic acid 2-glucoside powder obtained in Experiment 1, stirred, mixed, allowed to stand at ambient temperature for three days in an open system without covering the tray with a lid, and resulted in precipitating crystals in a block clump. The block clump was pulverized in a mortar and dried in vacuo at ambient temperature to obtain an about 200 g crystalline powder. The purity of ascorbic acid 2-glucoside of the crystalline powder was 99.2% by weight when measured on the HPLC disclosed in Experiment 2-2, while the moisture content was 2.8% by weight when measured on the Karl Fischer's method. When subjected to the powder X-ray diffractometry disclosed in Experiment 2-3, the crystalline powder gave a powder X-ray diffraction pattern of hydrous crystalline ascorbic acid 2-glucoside similarly as in FIG. 2 but no diffraction peak inherent to anhydrous crystalline ascorbic acid 2-glucoside was observed. The result indicates that a hydrous crystalline ascorbic acid 2-glucoside powder is efficiently obtained from an aqueous solution containing a relatively-high purity ascorbic acid 2-glucoside when hydrous crystalline ascorbic acid 2-glucoside is used as a seed crystal.

<Experiment 4: Preparation of Hydrous Crystalline Ascorbic Acid 2-Glucoside Powder from Amorphous Ascorbic Acid 2-Glucoside Powder>

Conversion from an amorphous ascorbic acid 2-glucoside powder into a hydrous crystalline ascorbic acid 2-glucoside powder was tried using the hydrous crystalline ascorbic acid 2-glucoside powder obtained in Experiment 3 as a seed crystal.

<Experiment 4-1: Preparation of Amorphous Ascorbic Acid 2-Glucoside Powder>

Two hundred grams of "AA2G", a product name of a commercialized particulate composition containing anhydrous crystalline ascorbic acid 2-glucoside with a purity of at least 98% by weight, commercialized by Hayashibara Biochemical Laboratories, Inc., Okayama, Japan, was completely dissolved in 2,000 ml of refined water, freeze-dried in vacuo over three days, and dried in vacuo overnight at a temperature of 40° C. or lower to obtain an about 200 g ascorbic acid 2-glucoside powder. The purity of ascorbic acid 2-glucoside of the powder was 98.7% by weight when determined on the HPLC disclosed in Experiment 2-2, while the moisture content of the powder was 1.5% by weight when determined on the Karl Fischer's method. When subjected to the powder X-ray diffractometry disclosed in Experiment 2-3, the powder was observed as a bunchy baseline in the powder X-ray diffraction pattern specific to amorphous powder, but no diffraction peak specific to anhydrous crystalline ascorbic acid 2-glucoside and hydrous crystalline ascorbic acid 2-glucoside. From the result, the powder was confirmed to be an amorphous ascorbic acid 2-glucoside powder.

<Experiment 4-2: Preparation of Hydrous Crystalline Ascorbic Acid 2-Glucoside Powder from Amorphous Ascorbic Acid 2-Glucoside Powder>

The amorphous ascorbic acid 2-glucoside powder obtained in Experiment 4-1 and the hydrous crystalline ascorbic acid 2-glucoside powder obtained in Experiment 3 were respectively mixed in a weight ratio of 9:1, 8:2, 7:3, 6:4 or 5:5, ground to homogeneity in a mortar and mixed. The resulting each powder was placed in "TEMP.&HUMID. CHAMBER PR-4K", a thermo-hygrostat, commercialized by ESPEC Corp., Osaka, Japan, and allowed to stand at a temperature of 25° C. and a relative humidity of 90% for 24 hours. Thereafter, each powder was taken out from the thermo-hygrostat and subjected to the powder X-ray diffractometry disclosed in Experiment 2-3 to obtain respective powder X-ray diffraction patterns. The obtained powder X-ray diffraction patterns were crosschecked with the powder X-ray diffraction patterns of hydrous crystalline ascorbic acid 2-glucoside and anhydrous crystalline ascorbic acid 2-glucoside (FIGS. 2 and 3) to judge the crystalline morphology of each powder. The results are in Table 1.

TABLE 1

| Mixture ratio of ascorbic acid 2-glucoside powders (weight ratio) | | Powder X-ray diffraction pattern of |
| --- | --- | --- |
| Amorphous powder | Hydrous crystalline powder | a powder after allowing it to stand at a temperature of 25° C. and a relative humidity of 90% for 24 hours |
| 9 | 1 | Mixture of anhydrous crystalline ascorbic acid 2-glucoside and hydrous crystalline ascorbic acid 2-glucoside |
| 8 | 2 | Mixture of anhydrous crystalline ascorbic acid 2-glucoside and hydrous crystalline ascorbic acid 2-glucoside |
| 7 | 3 | Only hydrous crystalline ascorbic acid 2-glucoside |
| 6 | 4 | Only hydrous crystalline ascorbic acid 2-glucoside |
| 5 | 5 | Only hydrous crystalline ascorbic acid 2-glucoside |

As shown in Table 1, the powders prepared by mixing the amorphous ascorbic acid 2-glucoside powder and the hydrous crystalline ascorbic acid 2-glucoside powder in the weight ratios of 7:3, 6:4 and 5:5 were completely converted into powders which exhibited the powder X-ray diffraction pattern of hydrous crystalline ascorbic acid 2-glucoside when retained at a temperature of 25° C. and a relative humidity of 90% for 24 hours. While, the powders prepared by mixing and coexisting the amorphous ascorbic acid 2-glucoside powder and the hydrous crystalline ascorbic acid 2-glucoside powder in the weight ratios of 9:1 and 8:2 gave the powder X-ray diffraction patterns where those of anhydrous crystalline ascorbic acid 2-glucoside and hydrous crystalline ascorbic acid 2-glucoside coexisted, and had been converted into powders where amorphous ascorbic acid 2-glucoside and hydrous crystalline ascorbic acid 2-glucoside coexisted. The result indicates that a hydrous crystalline ascorbic acid 2-glucoside powder can be produced from an amorphous ascorbic acid 2-glucoside powder by mixing the amorphous ascorbic acid 2-glucoside powder with the hydrous crystalline ascorbic acid 2-glucoside powder in an amount of at least 30% by weight of the total amount, and retaining the mixture at a temperature of 25° C. and a relative humidity of 90% for at least 24 hours.

<Experiment 5: Crystallization from Solution Containing Ascorbic Acid 2-Glucoside>

In accordance with a conventional process for producing a particulate composition obtaining anhydrous crystalline ascorbic acid 2-glucoside, a solution containing ascorbic acid 2-glucoside was prepared for investigating the process for producing a particulate composition containing hydrous crystalline ascorbic acid 2-glucoside.

<Experiment 5-1: Preparation of Solution Containing Ascorbic Acid 2-Glucoside>

To seven parts by weight of liquefied potato starch was added three parts by weight of L-ascorbic acid, and the resulting mixture was adjusted to pH 5.5 and to give a solid concentration of 30% w/v for use as a substrate solution. To the substrate solution was added a crude CGTase solution derived from a microorganism of the species *Geobacillus stearothermophilus*, commercialized by Hayashibara Co., Ltd., Okayama, Japan, in an amount of 100 units/g starch, d.s.b., enzymatically reacted at 55° C. for 40 hours to effect glucosyl transferation to L-ascorbic acid and to form ascorbic acid 2-glucoside and 2-O-α-glycosyl-L-ascorbic acids.

The enzymatic reaction solution thus obtained was heated to inactivate the remaining CGTase, adjusted to pH 4.5, admixed with "GLUCZYME AF6", a product name of a glucoamylase specimen commercialized by Amano Enzyme Inc., Aichi, Japan, in an amount of 50 units/g starch, d.s.b., and treated at 55° C. for 24 hours to hydrolyze 2-O-α-glycosyl-L-ascorbic acids up to ascorbic acid 2-glucoside and hydrolyze the coexisted saccharides up to glucose. The ascorbic acid 2-glucoside content of the enzymatic reaction solution was 30.4% by weight, d.s.b.

The enzymatic reaction solution was heated to inactivate the remaining glucoamylase, decolored and filtered with an activated charcoal, and desalted with a cation-exchange resin ($H^+$-form), followed by allowing L-ascorbic acid and ascorbic acid 2-glucoside to adsorb on an anion-exchange resin ($OH^-$-form) and washing the resin with water to remove most glucose. The ascorbic acid 2-glucoside and L-ascorbic acid adsorbed on the resin were eluted with 0.5 N hydrochloric acid solution, subjected to a gel filtration column chromatography using "DOWEX 50WX4" ($Ca^{2+}$-form), a product name of a strong-acid cation exchange resin commercialized by Dow Chemical Company, to collect a fraction rich in ascorbic acid 2-glucoside. The composition of the collected solution containing ascorbic acid 2-glucoside was 92.0% by weight of ascorbic acid 2-glucoside, 0.8% by weight of L-ascorbic acid, and 6.5% by weight of glucose, and 0.7% by weight of others, d.s.b.

<Experiment 5-2: Preparation of Particulate Composition Containing Hydrous Crystalline Ascorbic Acid 2-Glucoside by Solid-Liquid Separation>

A solution containing ascorbic acid 2-glucoside obtained by the method in Experiment 5-1 was concentrated in vacuo into a concentrate with a concentration of about 50% w/v, placed in a crystallizer, admixed with the hydrous crystalline ascorbic acid 2-glucoside powder obtained in Experiment 3 as a seed crystal in an amount of one percent by weight to the solid contents of the concentrate, adjusted to 40° C., and crystallized while stirring gently over five days to obtain a massecuite containing hydrous crystalline ascorbic acid 2-glucoside.

The massecuite thus obtained was subjected to a basket-type centrifuge in usual manner, followed by collecting the precipitated hydrous crystalline ascorbic acid 2-glucoside, spraying a small amount of aqueous ethanol to the collected crystals for washing, and then ageing, pulverizing, and drying the crystals to obtain a particulate composition containing hydrous crystalline ascorbic acid 2-glucoside powder with an ascorbic acid 2-glucoside purity of 99.3% by weight.

<Experiment 5-3: Preparation of Particulate Composition Containing Hydrous Crystalline Ascorbic Acid 2-Glucoside by Block-Pulverization Method>

A solution containing ascorbic acid 2-glucoside obtained by the method in Experiment 5-1 was concentrated in vacuo into a concentrate with a concentration of about 60% w/v, which was then transferred to a plastic tray (80 by 30 cm and 30 cm high), admixed with the hydrous crystalline ascorbic acid 2-glucoside powder obtained in Experiment 1 in an amount of two percent by weight to the solid contents of the concentrate, stirred, mixed, and allowed to stand at 45° C. for four days under the conditions without covering the plastic tray with a lid to effect crystallization and to prepare a block of hydrous crystalline ascorbic acid 2-glucoside. The formed block was cracked with a hammer, pulverized with "OSTER BLENDER ST-2", a product name of a blender commercialized by Osaka Chemical Co., Ltd., Osaka, Japan, dried in vacuo at ambient temperature to obtain a particulate composition containing hydrous crystalline ascorbic acid 2-glucoside. The purity of ascorbic acid 2-glucoside in the obtained particulate composition containing hydrous crystalline ascorbic acid 2-glucoside was 91.8% by weight.

<Experiment 6: Tabletting Property of Particulate Composition Containing Hydrous Crystalline Ascorbic Acid 2-Glucoside>

The tabletting property of a particulate composition containing hydrous crystalline ascorbic acid 2-glucoside of the present invention was investigated by the following method and compared with that of a conventional particulate composition containing anhydrous crystalline ascorbic acid 2-glucoside.

A hydrous crystalline ascorbic acid 2-glucoside powder with an ascorbic acid 2-glucoside purity of 99.2% by weight, obtained by the method in Experiment 3, was sieved to collect a powder with a particle size ranging from 53 to 106 μm. The powder thus obtained was placed in a metallic mold for tabletting (11 mm diameter and 30 mm thickness) in an amount of 0.4 g, and tabletted by loading on the powder one ton for 30 sec using "SSP-10A", a portable press machine, commercialized by Shimadzu Corp., Kyoto, Japan, followed by taking out the resulting tablets by releasing the load. The procedure was repeated 10 times to prepare 10 tablets in total. As a control, "AA2G", a trade mark of a commercialized particulate composition containing anhydrous crystalline ascorbic acid 2-glucoside with a purity of at least 98%, commercialized by Hayashibara Biochemical Laboratories, Inc., Okayama, Japan, was used to prepare a powder with a particle size ranging from 53 to 106 μm, which was then prepared into 10 tablets by the same method as above. The 10 tablets for each preparation were respectively observed their forms (cracking or chipping) and judged as "Tabletting property: Impassable" (X), where cracking or chipping were observed in at least one out of ten tablets; and "Tabletting property: Passable" (◯), where neither cracking nor chipping was observed in 10 tablets. The result is in Table 2.

TABLE 2

| Crystalline powder | Tabletting property | Tablet form |
|---|---|---|
| Particulate composition containing anhydrous crystalline ascorbic acid 2-glucoside (Control) | X | Cracking or chipping was observed in 9 out of 10 tablets |
| Particulate composition containing hydrous crystalline ascorbic acid 2-glucoside (The present invention) | ◯ | Neither cracking nor chipping was observed in any of 10 tablets |

As shown in Table 2, since cracking or chipping was observed in 9 out of 10 tablets with the particulate composition containing anhydrous crystalline ascorbic acid 2-glucoside as a control, the particulate composition was inferior in tabletting property. During the preparation of tablets, the particulate composition was frequently observed, as a causative of cracking, to be adhered to a cylinder (punch) of the portable press machine at the stage of releasing the load and it induced cracking at the stage of taking out from the metallic mold of the press machine. While, in the particulate composition containing hydrous crystalline ascorbic acid 2-glucoside of the present invention, neither cracking nor chipping was observed in all the 10 tablets and this revealed that the particulate composition is superior in tabletting property. When measured for hardness on "RHEOMETER CR-500DX", a product name of a rheometer commercialized by Sun Scientific Co., Ltd., Tokyo, Japan, the tablet prepared with the particulate composition containing hydrous crystalline ascorbic acid 2-glucoside had a degree of hardness of about 90 N. The results indicate that the particulate composition containing hydrous crystalline ascorbic acid 2-glucoside of the present invention is superior in tabletting property or formativeness to the particulate composition containing anhydrous crystalline ascorbic acid 2-glucoside and it is useful as a base material for preparing a tablet with a relatively high hardness.

<Experiment 7: Oil-Holding Capacity of Particulate Composition Containing Hydrous Crystalline Ascorbic Acid 2-Glucoside>

Using a particulate composition containing hydrous crystalline ascorbic acid 2-glucoside obtained by the method in Experiment 3-2, the oil-holding capacity of the particulate composition was determined. As a control, "AA2G", a product name of a commercialized particulate composition containing anhydrous crystalline ascorbic acid 2-glucoside with a purity of at least 98% by weight, commercialized by Hayashibara Biochemical Laboratories, Inc., Okayama, Japan, was used.

The measurements for oil-holding capacity of the particulate compositions were conducted as follows in accordance with the method disclosed in Japanese Patent Kokai No. 31650/84. Five grams of a corn oil (a reagent grade specimen, Lot No.: WKL1215, commercialized by Wako Pure Chemical Industries, Osaka, Japan, was placed in a 50-ml plastic container, to which was gradually added while stirring the particulate composition containing hydrous crystalline ascorbic acid 2-glucoside or the particulate composition containing anhydrous crystalline ascorbic acid 2-glucoside, both of which had been adjusted to give a particle size of 53 to 106 μm similarly as in Experiment 6. Although the resulting mixture retains a free-flowing ability while the additive amount of any of the particulate compositions is relatively low, but it increases its viscosity as the increase of the additive amount and becomes a clump in due course. As the additive amount further increases, the clump increases its hardness and finally it could not keep together and begins to be unstiffen. The moment was regarded as the end point and the oil-holding capacity was determined by the following equation based on the amount of each crystalline particulate composition that had been added until the end point. The result is in Table 3.

$$\text{Oil-holding capacity} = \frac{\text{Corn oil (5 g)}}{\text{Additive amount of crystalline particulate composition (g)}} \times 100 \quad \text{[Equation 1]}$$

TABLE 3

| Crystalline particulate composition | Oil-holding capacity |
|---|---|
| Particulate composition containing anhydrous crystalline ascorbic acid 2-glucoside (Control) | 25.2 |
| Particulate composition containing hydrous crystalline ascorbic acid 2-glucoside (The present invention) | 38.3 |

As evident from Table 3, the oil-holding capacity of the particulate composition containing anhydrous crystalline ascorbic acid 2-glucoside as a control was 25.2, while that of the particulate composition containing hydrous crystalline ascorbic acid 2-glucoside was 38.3 as high as about 1.5-folds of that of the former. The result indicates that the particulate composition containing hydrous crystalline ascorbic acid 2-glucoside has a higher lipophilicity than the particulate composition containing anhydrous crystalline ascorbic acid 2-glucoside and the former as the present invention is more useful as a base material for pulverizing oleosus substances than the latter.

The present invention is explained in more detail with reference to the following Examples but it should never be restricted thereby.

Example 1

Particulate Composition Containing Hydrous Crystalline Ascorbic Acid 2-Glucoside Ten kilograms of "AA2G", a product name of a commercialized particulate composition containing anhydrous crystalline ascorbic acid 2-glucoside with a purity of at least 98% by weight, commercialized by Hayashibara Biochemical Laboratories, Inc., Okayama, Japan, was added to 10 L of refined water and completely dissolved therein by stirring. To the solution was added 100 g of a particulate composition containing hydrous crystalline ascorbic acid 2-glucoside obtained by the method in Experiment 3, stirred, mixed, distributed to three plastic containers with a size of 30 by 60 cm and 40 cm high, allowed to stand at 50° C. for three days under an open system without covering the plastic containers with lids to effect crystallization, and aged at ambient temperature for another one day. The resulting block clump of crystals was pulverized in usual manner and dried at 30° C. to produce an about 9.7 kg particulate composition containing hydrous crystalline ascorbic acid 2-glucoside. When measured on the HPLC disclosed in Experiment 2-2, the particulate composition had an ascorbic acid 2-glucoside purity of 98.4% by weight and had a moisture content of 3.0% by weight when determined on the Karl Fischer's method.

The product has a satisfactory free-flowing ability and it can be advantageously extensively used in compositions such as food products, cosmetics, quasi-drugs, and pharmaceuticals as an acid-imparting agent, taste-improving agent, filler/diluent/excipient/vehicle/adjuvant, and base material for pulverizing oleosus substances.

Example 2

Particulate Composition Containing Hydrous Crystalline Ascorbic Acid 2-Glucoside Seven parts by weight of tapioca starch was added to 25 parts by weight of water, admixed with a commercialized liquefying enzyme, dissolved by heating, admixed with three parts by weight of L-ascorbic acid, and adjusted to pH 5.5 for use as a substrate solution. A crude enzyme solution of a CGTase derived from a microorganism of the species *Geobacillus stearothermophilus*, commercialized by Hayashibara Co., Ltd., Okayama, Japan, in an amount of 100 units/g tapioca starch, d.s.b., and enzymatically reacted at 55° C. for 50 hours to form ascorbic acid 2-glucoside and 2-O-α-D-glycosyl-L-ascorbic acids.

The enzymatic reaction solution was heated to inactivate the remaining enzyme, adjusted to pH 4.5, admixed with "GLUCOZYME #20000", a product name of a glucoamylase specimen, 20,000 units/g, commercialized by Nagase ChemteX Corp., Osaka, Japan, in an amount of 50 units/g starch, d.s.b., and enzymatically reacted at 55° C. for 24 hours to hydrolyze 2-O-α-glycosyl-L-ascorbic acids up to ascorbic acid 2-glucoside and to hydrolyze concomitant saccharides up to glucose. The ascorbic acid 2-glucoside content in the enzymatic reaction solution was about 30.5% by weight, d.s.b.

The enzymatic reaction solution was heated to inactivate the remaining enzyme and decolored and filtered with an activated charcoal, and the filtrate was desalted with a cation-exchange resin ($H^+$-form) and subjected to an anion-exchange resin ($OH^-$-form) to adsorb L-ascorbic acid and ascorbic acid 2-glucoside on the resin, followed by washing the resin with water to remove most of glucose, feeding 0.5 N hydrochloric acid solution to the resin to effect elution, subjecting the eluate to a gel filtration column chromatography using "DOWEX 50WX4" ($Ca^{2+}$-form), a product name of a strong-acid cation-exchange resin, commercialized by Dow Chemical Co., Midland, USA, and collecting a fraction rich in ascorbic acid 2-glucoside. The collected solution containing ascorbic acid 2-glucoside had a composition of 89.3% by weight of ascorbic acid 2-glucoside, 1.2% by weight of L-ascorbic acid, 7.8% by weight of glucose, and 1.7% by weight of others, d.s.b.

The solution containing ascorbic acid 2-glucoside was concentrated in vacuo to give a solid concentration of about 60%, d.s.b., and the concentrate was placed in a crystallizer, admixed with a hydrous crystalline ascorbic acid 2-glucoside powder obtained by the method in Experiment 3 in an amount of two percent to the weight of the solid contents, d.s.b., adjusted to 40° C., and gently stirred for five days to effect crystallization to obtain a massecuite with precipitated hydrous crystalline ascorbic acid 2-glucoside. The massecuite was in usual manner subjected to a basket-type centrifuge to collect crystals, which were then sprayed with a small amount of refined water for washing, pulverized, and dried to obtain a particulate composition containing hydrous crystalline ascorbic acid 2-glucoside. The product had an ascorbic acid 2-glucoside purity of 98.5% by weight, d.s.b.

The product has a satisfactory free-flowing ability and it can be advantageously extensively used in compositions such as food products, cosmetics, quasi-drugs, and pharmaceuticals as an acid-imparting agent, taste-improving agent, filler/diluent/excipient/vehicle/adjuvant, and base material for pulverizing oleosus substances.

Example 3

Particulate Composition Containing Hydrous Crystalline Ascorbic Acid 2-Glucoside A fraction rich in ascorbic acid 2-glucoside was collected through an enzymatic reaction and purification by the same method as in Example 2, except for replacing tapioca starch with corn starch. The collected solution containing ascorbic acid 2-glucoside had a composition of 85.4% by weight of ascorbic acid 2-glucoside, 3.8% by weight of L-ascorbic acid, 8.7% by weight of glucose, and 2.1% by weight of others, d.s.b.

The solution containing ascorbic acid 2-glucoside was concentrated in vacuo to give a solid concentration of about 76%, d.s.b., placed in a crystallizer, admixed with a hydrous crystalline ascorbic acid 2-glucoside powder obtained by the method in Example 1 in an amount of two percent to the weight of the solid contents, d.s.b., adjusted to 40° C., stirred, mixed, poured into a plastic container with 30 by 40 cm and 30 cm high, subjected to crystallization at 50° C. for three days under an open system without covering the plastic container with a lid, and aged at ambient temperature for another one day. The resulting block lump of crystals was cracked with a hammer, pulverized in usual manner, and dried at 30° C. to produce a particulate composition containing hydrous crystalline ascorbic acid 2-glucoside. The product contained 85.2% by weight of ascorbic acid 2-glucoside, 3.9% by weight of L-ascorbic acid, and 8.8% by weight of glucose.

The product has a satisfactory free-flowing ability and it can be advantageously extensively used in compositions such as food products, cosmetics, quasi-drugs, and pharmaceuticals as an acid-imparting agent, taste-improving agent, filler/diluent/excipient/vehicle/adjuvant, and base material for pulverizing oleosus substances.

Example 4

Tablet

One hundred parts by weight of a particulate composition containing hydrous crystalline ascorbic acid 2-glucoside obtained by the method in Example 1, 1.3 parts by weight of calcium pantothenate, and 0.2 part by weight of riboflavin were mixed to homogeneity, and the resulting powder was in usual manner subjected to a tabletting machine to obtain tablets, 0.5 g each. Similarly as commercialized vitamin C tablets, the product can be advantageously used as a vitamin-C-supplementing tablet for use in physical exhaustion and declined physical strength.

Example 5

Vitamin-E-Containing Powder

To one part by weight of "γ70", a product name of an oily natural tocopherol commercialized by J-Oil Mills, Inc., Tokyo, Japan, was added five parts by weight of a particulate composition containing hydrous crystalline ascorbic acid 2-glucoside obtained by the method in Example 1, and the mixture was mixed by a universal mixer, allowed to stand overnight, and pulverized to prepare a powder containing vitamin E (tocopherol) The product can be suitably used as a supplement consisting of vitamin E and stable vitamin C.

Example 6

Milky Lotion

One part by weight of avocado oil, one part by weight of tetraoleic acid polyoxyethylene sorbitol, one part by weight of lipophilic monostearic glycerol, one part by weight of a particulate composition containing hydrous crystalline ascorbic acid 2-glucoside obtained by the method in Example 1, 0.5 part by weight of polyoxyethylene behenyl ether, 0.5 part by weight of pyruvic acid, 0.5 part by weight of behenyl alcohol, and adequate amounts of vitamin E and an antiseptic were dissolved by heating in usual manner, followed by adding to the resulting solution five parts by weight of 1,3-butylene glycol, one part by weight of sodium L-lactate, 0.1 part by weight of carboxyvinylpolymer, and 85.3 parts by weight of refined water, homogeneously stirring the mixture with a homogenizer to effect emulsification. The emulsion was further admixed with an adequate amount of a flavor and mixed again by stirring to produce a milky lotion. The product can be advantageously used as a skin-beautifying agent, skin-whitening agent, sunscreen, etc.

INDUSTRIAL APPLICABILITY

The hydrous crystalline ascorbic acid 2-glucoside of the present invention is in the form of a novel crystalline ascorbic acid 2-glucoside that has not been known so far. The particulate composition containing hydrous crystalline ascorbic acid 2-glucoside of the present invention is superior in free-flowing ability and it has the merit of providing a tablet with a relatively-high hardness that could not have been produced with conventional particulate compositions containing anhydrous crystalline ascorbic acid 2-glucoside, when used as a filler/diluent/excipient/vehicle/adjuvant. In addition, the particulate composition containing hydrous crystalline ascorbic acid 2-glucoside of the present invention has an improved lipophilicity compared to conventional particulate compositions containing anhydrous crystalline ascorbic acid 2-glucoside and it can be advantageously used as a base material for pulverizing oily substances. The present invention is surely a significant invention that not only has an academic significance as in such a conventionally unknown discovery of hydrous crystalline ascorbic acid 2-glucoside but also greatly contributes to the fields of food products, cosmetics, quasi-drugs, and pharmaceuticals.

The invention claimed is:

1. A hydrous crystalline 2-O-α-D-glucosyl-L-ascorbic acid comprising crystallization water.

2. The hydrous crystalline 2-O-α-D-glucosyl-L-ascorbic acid of claim 1, which exhibits diffraction peaks at least at diffraction angles (2θ) of 6.1°, 9.2°, 10.6°, 11.4° and 12.1° in a powder X-ray diffraction pattern obtained by using a CuKα-ray as an X-ray source.

3. The hydrous crystalline 2-O-α-D-glucosyl-L-ascorbic acid of claim 1, which contains about 2.7% by weight of crystallization water.

4. The hydrous crystalline 2-O-α-D-glucosyl-L-ascorbic acid of claim 1, which exhibits an endothermic peak at around 156° C. when determined on differential scanning calorimetric analysis.

5. A particulate composition comprising hydrous crystalline 2-O-α-D-glucosyl-L-ascorbic acid, which comprises the hydrous crystalline 2-O-α-D-glucosyl-L-ascorbic acid of claim 1, wherein the purity of 2-O-α-D-glucosyl-L-ascorbic acid is at least 85% by weight, on a dry solid basis.

6. A process for producing the hydrous crystalline 2-O-α-D-glucosyl-L-ascorbic acid of claim 1, which comprises a step of evaporating water from an aqueous solution comprising a supersaturated amount of 2-O-α-D-glucosyl-L-ascorbic acid and a coexisting anhydrous crystalline 2-O-α-D-glucosyl-L-ascorbic acid to crystallize the hydrous crystalline 2-O-α-D-glucosyl-L-ascorbic acid of claim 1.

7. A process for producing the hydrous crystalline 2-O-α-D-glucosyl-L-ascorbic acid of claim 1, which comprises the steps of adding said hydrous crystalline 2-O-α-D-glucosyl-L-ascorbic acid of claim 1 as a seed crystal to an aqueous solution comprising 2-O-α-D-glucosyl-L-ascorbic acid to precipitate hydrous crystalline 2-O-α-D-glucosyl-L-ascorbic acid; and collecting the precipitated crystal.

8. A process for producing a hydrous crystalline 2-O-α-D-glucosyl-L-ascorbic acid of claim 1, which comprises the steps of coexisting the hydrous crystalline 2-O-α-D-glucosyl-L-ascorbic acid of claim 1, as a seed crystal, with an amorphous 2-O-α-D-glucosyl-L-ascorbic acid powder; retaining the resulting mixture at a temperature of 25° C. and a relative humidity of 90% to precipitate hydrous crystalline 2-O-α-D-glucosyl-L-ascorbic acid; and collecting the precipitated crystal.

9. A filler/diluent/excipient/vehicle/adjuvant, which consists of a member selected from the group consisting of hydrous crystalline 2-O-α-D-glucosyl-L-ascorbic acid comprising crystallization water, and the particulate composition of claim 5.

10. A base material for pulverizing oily substances, which consists of a member selected from the group consisting of hydrous crystalline 2-O-α-D-glucosyl-L-ascorbic acid comprising crystallization water, and the particulate composition of claim 5.

11. A process for producing a food product, cosmetic, quasi-drug, or pharmaceutical, which contains a step of incorporating a member selected from the group consisting of hydrous crystalline 2-O-α-D-glucosyl-L-ascorbic acid comprising crystallization water, and the particulate composition of claim 5.

* * * * *